(12) United States Patent
Gordon

(10) Patent No.: US 6,911,018 B2
(45) Date of Patent: Jun. 28, 2005

(54) SAFETY SYRINGE

(75) Inventor: Dennis Gordon, Las Vegas, NV (US)

(73) Assignee: Cosmetic and Medical Inventions, LLC, La Mirada, CA (US)

( * ) Notice: Subject to any disclaimer, the term of this patent is extended or adjusted under 35 U.S.C. 154(b) by 144 days.

(21) Appl. No.: 10/350,961

(22) Filed: Jan. 24, 2003

(65) Prior Publication Data

US 2004/0030300 A1 Feb. 12, 2004

Related U.S. Application Data

(60) Provisional application No. 60/401,742, filed on Aug. 6, 2002.

(51) Int. Cl.$^7$ .............................. A61M 5/00; A61M 5/32
(52) U.S. Cl. ....................... 604/110; 604/197; 604/198; 128/919
(58) Field of Search .............................. 604/93.01, 110, 604/187, 192, 197, 198, 218, 227, 239, 240, 241, 243; 128/919

(56) References Cited

U.S. PATENT DOCUMENTS

| 5,163,907 | A | | 11/1992 | Szuszkiewicz |
| 5,205,824 | A | * | 4/1993 | Mazur ........................ 604/110 |
| 5,267,962 | A | | 12/1993 | Jenson |
| 5,380,285 | A | | 1/1995 | Jenson |
| 5,540,660 | A | * | 7/1996 | Jenson ........................ 604/110 |
| 6,432,082 | B1 | * | 8/2002 | Chen .......................... 604/110 |

\* cited by examiner

*Primary Examiner*—Brian L. Casler
*Assistant Examiner*—Mark K Han
(74) *Attorney, Agent, or Firm*—Knobbe Martens Olson & Bear, LLP

(57) ABSTRACT

A hypodermic syringe provides a simple mechanism for manually retracting its needle into the syringe after injection has been completed. The syringe preferably has an elastomeric barrel to exert a radial bias to seal on a retractable needle carrier and the plunger. Attachment components on the plunger and needle carrier engage such that withdrawal of the plunger releases the needle carrier for withdrawal into the syringe barrel.

10 Claims, 5 Drawing Sheets

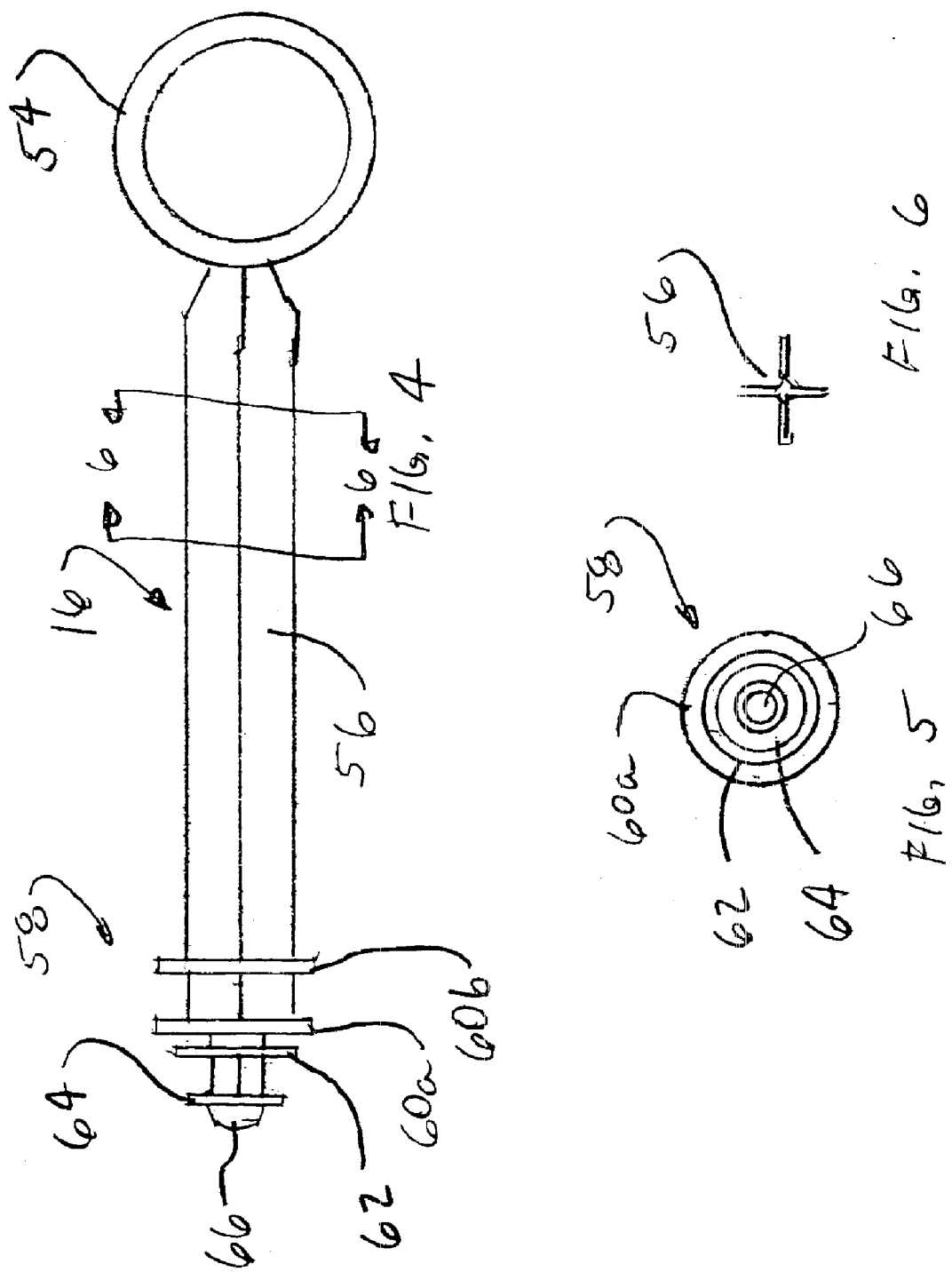

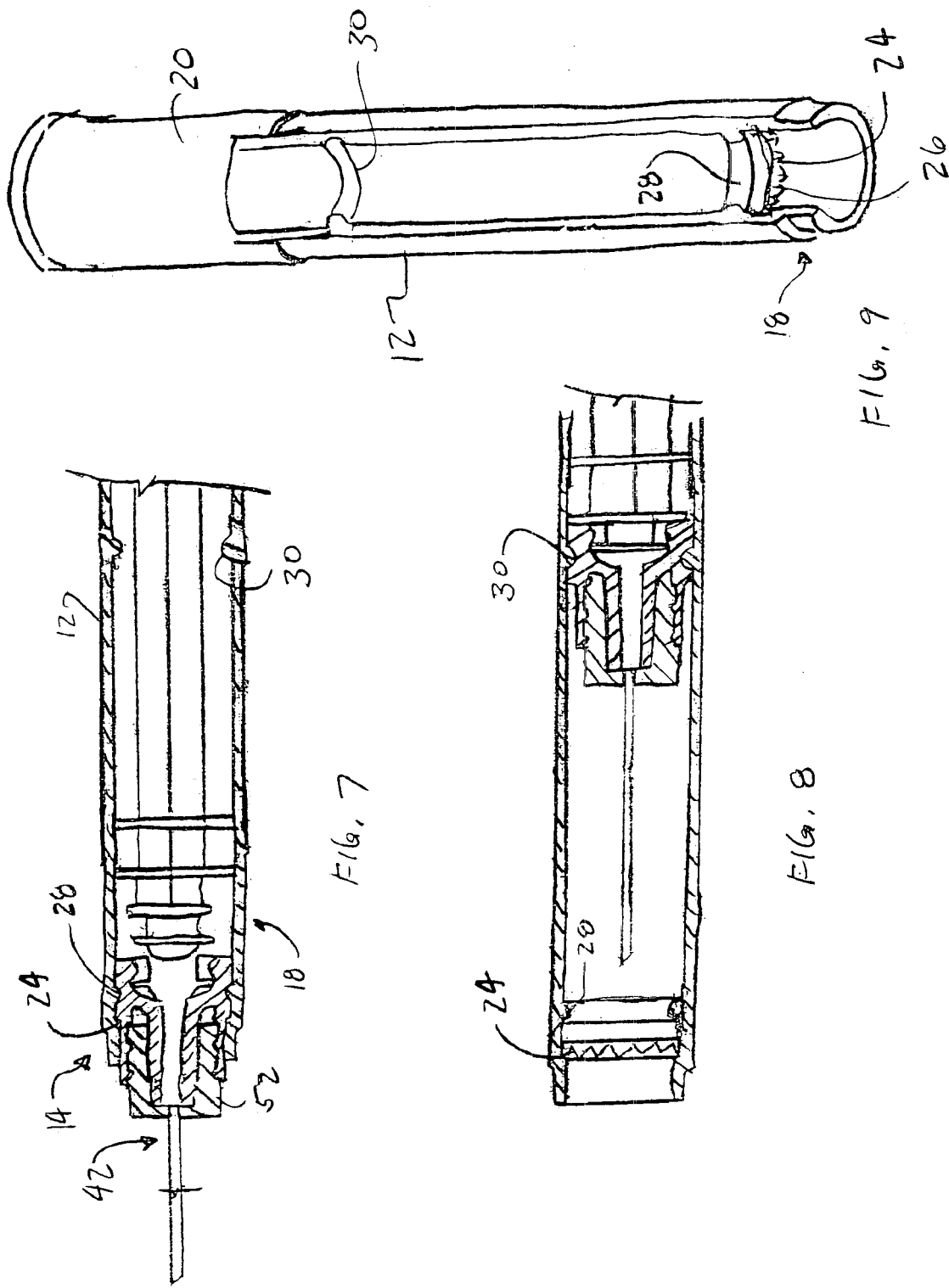

SAFETY SYRINGE

CROSS-REFERENCE TO RELATED APPLICATION

This application is a provisional conversion application and claims priority to commonly owned and prior filed provisional application No. 60/401,742 filed on Aug. 6, 2002 and entitled "Safety Syringe."

FIELD OF THE INVENTION

The present invention relates to medical devices and more particularly to hypodermic syringes designed to provide cross contamination protection to others by way of a retractable needle assembly that prevents accidental contact with the needle after use.

BACKGROUND OF THE INVENTION

Inadvertent needle stick injuries from used syringes may present a significant health hazard to others if infectious blood products are transmitted. Such accidental needle sticks may spread hepatitis, AIDS and other communicable diseases to health care workers and patients. In certain instances, the resulting disease may be life threatening. Further, the emotional distress from the fear of contracting such diseases can be significant. Still further, in the event of a stick, series of diagnostic blood tests may have to be performed to determine if cross-contamination has occurred in a needle stick injury. In many cases, the victim often is required to receive injections of gamma globulin to prevent further infection and to cure the patient. This is uncomfortable, inconvenient, and expensive to the victim.

According to the prior art, the usual technique has been to, after use of the needle, to break off the needle and dispose of the needle and syringe in a "sharps" container for secured disposal such as by incineration or stabilization in, for example, plastic of concrete.

Efforts have been made to develop syringes which attempt to prevent inadvertent sticks. In Chen, U.S. Pat. No. 6,432,082 issued Aug. 13, 2002, there is disclosed a safety syringe having a needle holder which is retractable into the barrel of the syringe. The needle holder is secured to the syringe barrel by a frangible component. After use, the uses forces the plunger to couple with the needle holder and withdraws the plunger to rupture the frangible component so that the portion of the holder mounting the needle (cannula) can be withdrawn into the barrel. A drawback of this design is that the frangible portion of membrane must be manufactured to tolerances such that (1) the pressure imposed by the plunger during aspiration of the medicine into or injection of the medicine out of the syringe does not rupture the seal and (2) still provide for rupturing the portion during withdrawal of the plunger without the plunger first separating from the needle holder. It is submitted that such requirements contribute to the expense of such a device. Further, the inability of the health card provider to rupture the portion will cause frustration and abandonment of the operation to withdraw the needle.

In Jenson, U.S. Pat. No. 5,540,660 issued Jul. 30, 1996 there is disclosed another syringe where a needle holder is captured by the plunger for withdrawal into the syringe barrel. In one embodiment of this disclosure, the plunger makes and interference fit into a tapered sleeve such that withdrawal of the plunger withdraws the sleeve and needle into the barrel. A drawback of this arrangement is that it would be difficult to aspirate medicine into the syringe without creating an interference fit between the plunger and sleeve thus disabling the syringe before injection of the medicine. In another embodiment an snap connection is utilized to couple the plunger to a needle holder. In either embodiment, close tolerances must be adhered to during manufacture to provide the seal between the sleeve and needle holder. Further, for either embodiment, an arcuate cannula is required to prevent re-use of the device.

Mazur, U.S. Pat. No. 5,205,824 issued Apr. 27, 1993 discloses another syringe where the needle holder is retained at the end of the syringe barrel only by the friction between the o-rings and the barrel which, it is believed, would (1) make secure attachment of the needle to the holder difficult since the holder may tend to rotate as the needle is threaded thereon. Further there remains a risk that insertion of he needle into a bottle of medicine for aspiration of medicine into the syringe would dislodge the needle holder and interfere with the seal.

There is a need for a safety syringe which is easy and inexpensive to manufacture, which provides for withdrawal of the needle into the barrel of the syringe, which can be re-used if desired, which has a positive coupling to provide for attachment of the needle and retention of the needle during aspiration and injection, which provides for a positive stop during withdrawal of the needle to indicate full withdrawal of the needle and which overcomes the drawbacks noted above.

SUMMARY OF THE INVENTION

There is, therefore, set forth according to the present invention, a safety hypodermic syringe designed to provide cross contamination protection to others by way of a retractable needle assembly obviating accidental contact with the needle to another person and which is of simple and inexpensive construction.

Toward this end the safety syringe is disclosed which includes a hollow barrel having a forward and rear end. Proximate the forward end a first retention structure is provided which may be in the form of a circumferential groove or ridge or other suitable structure. A first coupling structure is also provided at the first end. Proximate said rear end is a second retention structure which may also be in the form of a circumferential groove or ridge.

A needle carrier is disposed at said forward end and has a third retention structure configured to engage with the first retention structure to releaseably retain the needle carrier at the forward end and to engage the second retention structure to retain said needle carrier in a position withdrawn into the barrel. To prevent the needle carrier from rotating in the barrel at the first end, the barrel and needle carrier have cooperative coupling structures which may be embodied as engaging tabs or teeth. Also provided is a mounting for mounting a needle such as a threaded or luer lock connection as is known in the art.

A plunger is disposed in the barrel and has a head to slideably seal within the barrel for aspiration of fluid into an out of the barrel. At the head and at the needle carrier are cooperative attachment components which, when engaged, attach the needle carrier to the plunger for withdrawal thereof. Withdrawal of the plunger disengages the third retention structure from the first retention structure to release the needle carrier to be withdrawn a position in the barrel where the third retention structure engages the second retention structure to retain the needle carrier with its needle in the withdrawn position.

The barrel may be rigid but is preferably fashioned from an elastomeric material such as plastic or the like to be radially biased at least in the regions of the first and second retention structures for engagement with the third retention structure. The barrel may also be rigid with an elestomeric liner.

Accordingly, the health care provider positions the plunger adjacent the needle carrier and secures the needle to the needle carrier. The needle is inserted into a vial of fluid and the plunger is withdrawn to aspirate the fluid to be injected into the barrel. The needle is withdrawn from the vial and, for example, inserted into a patient. The plunger is pushed through the barrel to aspirate the fluid from the barrel through the needle into the patient. At the forward end the plunger is positioned such that the cooperative retention structures on the head and needle carrier engage to capture the needle carrier to the plunger. Thereafter the plunger is withdrawn disengaging the needle carrier from the forward end of the syringe barrel and continued withdrawal of the plunger withdraws the needle carrier and needle to a position nested within the barrel whereat the needle carrier engages the second retention structure to retain the needle carrier within the barrel. In this position the needle is safely withdrawn into the barrel to prevent inadvertent sticks. The syringe may then be disposed of in a sharps disposal container. If desired, the syringe may be sterilized and re-used.

DESCRIPTION OF THE DRAWINGS

These and other features and advantages will become better understood with reference to the description, claims and drawings wherein:

FIG. 4 is a side view of the plunger for the syringe of FIG. 1;

FIG. 5 is an end view of the plunger of FIG. 4;

FIG. 6 is a section view of the fluted shaft of the plunger of FIG. 6 taken along line 6—6;

FIG. 7 is a side section view of the syringe with the plunger in a first position;

FIG. 8 is a side section view showing capture of the needle carrier by the plunger and withdrawal into the barrel; and FIG. 9 is a perspective, partial cutaway view of the barrel for the syringe.

DESCRIPTION

Figure 1:
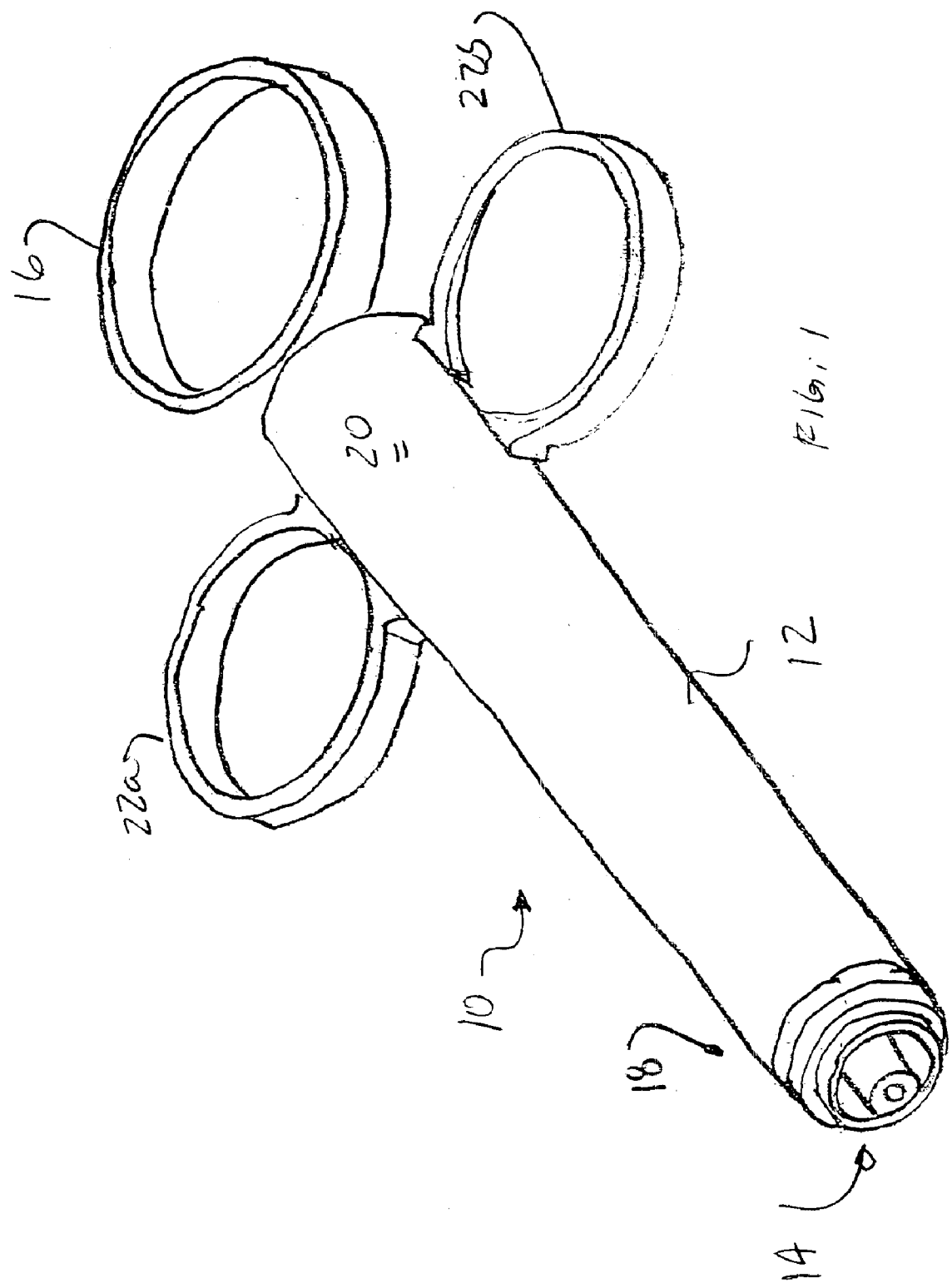
FIG. 1 is a front perspective view of the syringe without a needle.

Turning to the drawings, FIG. 1 shows the safety syringe 10 according to the present invention. The syringe 10 includes a barrel 12 which may be cylindrical and rigid such as by being manufactured from a hard plastic. Alternatively and preferably, the barrel may be constructed from an elastomeric or elastically deformable material such as such as vinyl, soft polyurethane or other elastically, radially biased, deformable plastic. The deformable plastic should be somewhat elastic but still able to retain its overall cylindrical shape and should be selected to withstand sterilization processes. Still alternatively, the barrel 12 may be rigid with an interior, elastic, lining. Thus, the elastic characteristic permits the barrel 12 to impose a radial bias against expansion and to be contractile to a degree.

To provide for aspiration of the desired amount of fluid, e.g. medicine, into the barrel 12, the barrel should transparent or semi-transparent and include graduation markings to indicate volume within the barrel 12.

The syringe 10 also includes a needle carrier 14, the details of which will hereafter be described.

To provide for aspiration of fluid into an out of the syringe barrel 12, the syringe 10 includes a plunger 16, the details of which will hereafter be described.

The barrel 12 is hollow and preferably cylindrical having a forward end 18 and rear end 20. At the rear end 20 a pair of finger loops 22a, b may be mounted to the barrel 12 to receive the fingers of the health care provider using the syringe 10.

With reference to FIGS. 3, and 7–9, the barrel 10 includes proximate the forward end 18 a rearward facing, circumferential shoulder 24 which defines a first coupling structure the purposes of which will hereinafter become evident. The shoulder 24 may have teeth 26, tabs, notches or other cooperative structure to engage with structure on the needle carrier 14 to prevent coaxial rotation thereof relative to the barrel 12.

Disposed rearward of the shoulder 24 inside the barrel 12 is a first retention structure 28 illustrated as one or more circumferentially arranged, radial projections fashioned within the barrel 12. As shown in the drawings, the first retention structure 28 may be a continuous, circumferential ridge or projection. Alternatively the first retention structure my be discontinuous.

Disposed proximate the rear end 20 of the barrel 12 and inside thereof is a second retention structure 30. The second retention structure 30 has a construction similar to the first retention structure 28. The second retention structure 30 is disposed such that, as hereinafter described, the needle carrier 14 and attached needle can be fully withdrawn into the barrel 12.

In an alternative embodiment, the first and second retention structures 28, 30 may be embodied as continuous or discontinuous circumferential grooves in the inside wall of the barrel 12.

Figure 2:
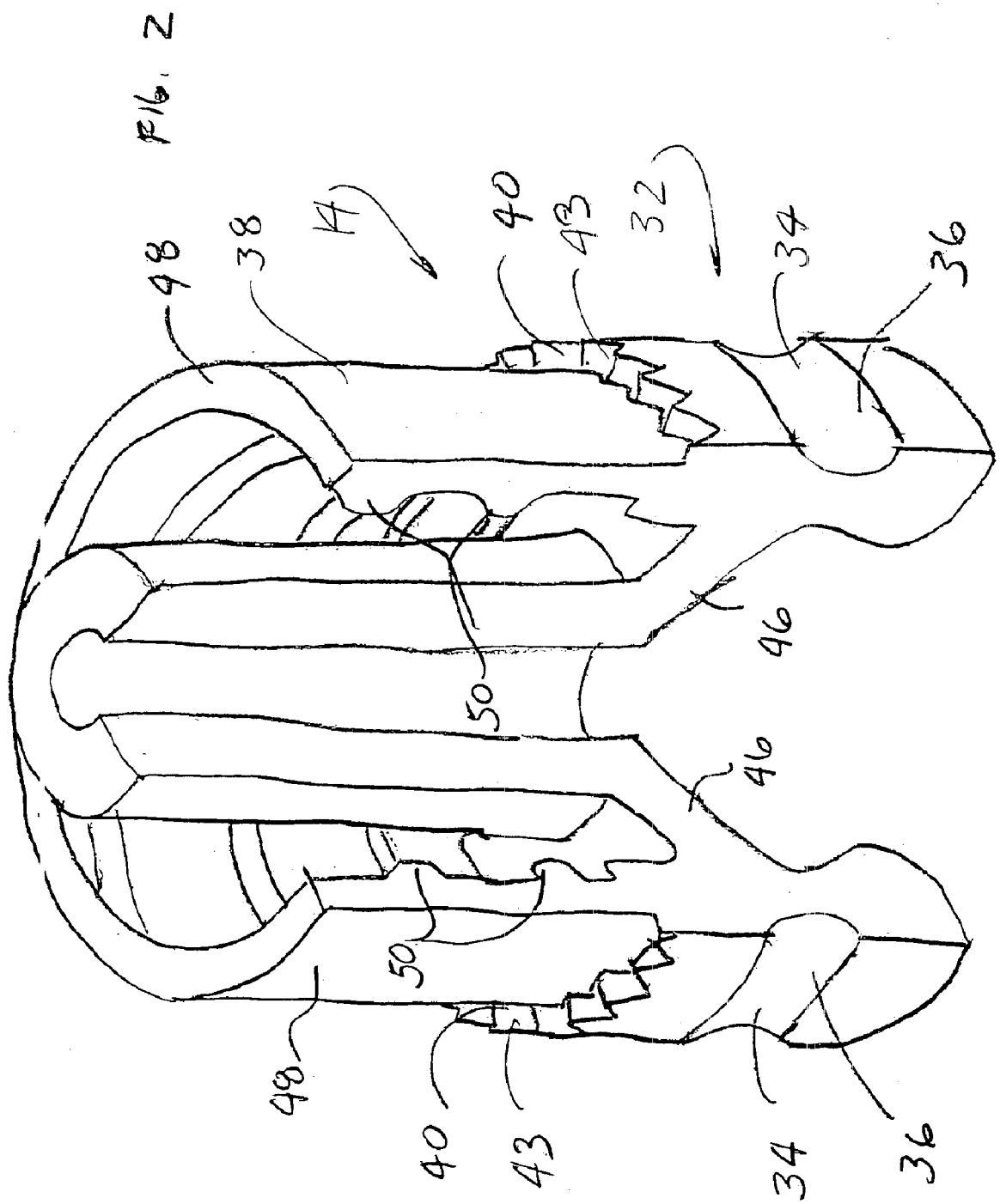
FIG. 2 is a side, perspective, partial section view of the needle carrier.
Figure 3:
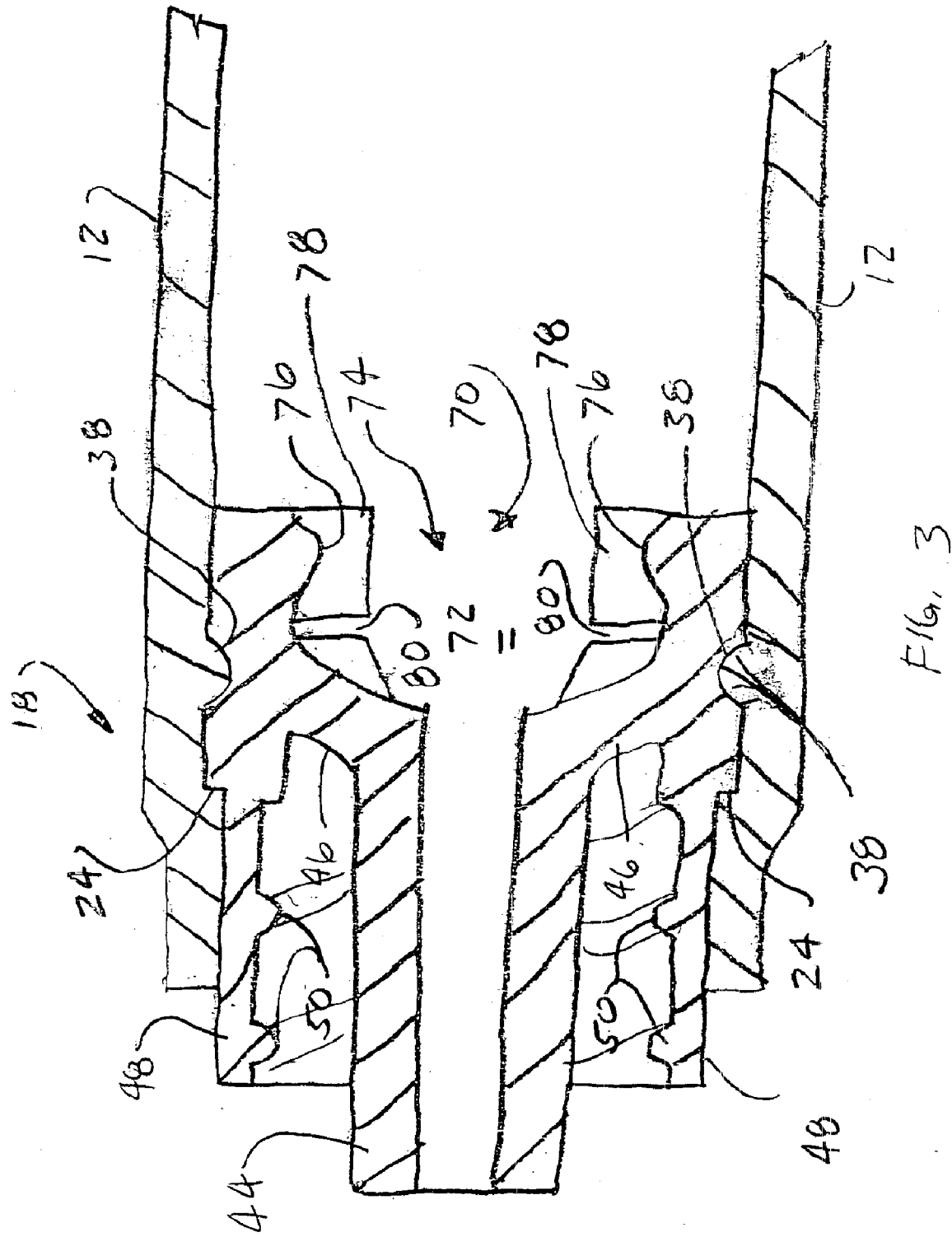
FIG. 3 is a side section view of the needle carrier mounted in the barrel of the syringe of FIG. 1.

Turning to FIGS. 2 and 3, an embodiment of the needle carrier 14 is shown. The needle carrier 14 is generally cylindrical to be received at the forward end 18 of the barrel 12. In a cylindrical first portion 32 there is disposed a third retention structure 34 shown as embodied as a circumferential depression 36 dimensioned to closely receive the first and second retention structures 28, 30 of the barrel 12 to releasably retain and capture the needle carrier 14 therein. Where the first and second retention structures 28, 30 are grooves or depressions, the third retention structure 34 would be a projection to be received into the grooves.

The first portion 32 transitions to a smaller diameter second portion 38 at a circumferential, axially and forwardly directed, surface 40 defining a second coupling structure. The surface 40 is cooperatively configured to engage with the first coupling structure of the shoulder 24 and its teeth 26 to couple the needle carrier 14 to the barrel 12 against axial rotation. Thus the surface 40 includes teeth 42 as well. It should be noted that the first and second coupling structures could have any suitable configuration for coupling thereof such as one or more interlocking tabs, pins, or the like.

At the forward end of the needle carrier there is defined a mounting structure suitable for mounting of a needle 42 (FIGS. 7 and 8) or cannula. Accordingly the forward end of the needle carrier includes an axially projecting, hollow, nipple 44. The nipple 44 is supported by a radial substrate 46 which extends to a cylindrical wall 48 which extends axially spaced from the nipple 44. The inside surface of the wall 48 includes threads 50. The needle 42 has an exteriorly threaded cap 52 which is received over the nipple 44 and is threaded into the wall 48 with cooperating threads. The cap 52 and threads 50 define a standard luer lock connection for the needle as is known in the art. As shown in FIG. 7, when the needle 42 is mounted to the needle carrier 14, a fluid passageway is defined through the nipple 44 and needle 42 for fluid to be aspirated into and from the syringe barrel 12 thought the needle 42.

Opposite the nipple 44 the needle carrier 14 has a first attachment component 70 adapted for coupling the needle carrier 14 to the plunger 16. With reference to FIG. 3, the first attachment component is defined as an ellipsoidal recess 72 defined in the needle carrier 14 and which intersects with the hollow of the nipple 44. The recess 72 opens to the inside of the barrel 12 through a reducing neck 74 defined by a circumferential, and radially inwardly directed nose 76. At spaced locations, e.g. at 90 degree intervals, radially directed, deformable wings 78 extend into the recess 72. Each wing includes a radial slot 80.

To provide for aspiration of fluid and for withdrawing the needle carrier 14, the syringe 10 also includes the plunger 16 as shown in FIGS. 4–6. The plunger 16 includes at one end a thumb loop 54 to receive the thumb of the health care provider for manipulation of the plunger 16. A shaft 56 extends between the thumb loop 54 and a plunger head 58. The shaft 56 may be orthogonally fluted or of any other suitable shape.

At the head 58 there are disposed axially spaced and radially extending first and second seals 60a, b which are, when the barrel 12 is rigid, elastically deformable to engage and seal against the inside surface of the barrel 12. Where the barrel 12 is elastomeric or includes an elastomeric lining the seals 60a, b may be rigid.

Forward of the seals 60a, b, the head 58 includes a radially extending stop 62. Forward of the stop 62 is a radially extending, deformable disk 64 of a size to (1) deform to pass through the neck 74 and to expand to engage into the slots 80 for coupling the needle carrier 14 to the plunger 16. The disk 64 defines a second attachment component for the syringe 10. Forward of the disk is an end piece 66 which is adapted to be received into the recess 72.

With the foregoing in mind the operation of the syringe 10 will now be described. The syringe 10 is assembled with the needle carrier 14 disposed in the forward end 18 of the barrel 12. In this position the first retention structure of the barrel, e.g. the radially projecting projection, is received into the depression of the needle carrier 14 defining the third retention structure. The elastomeric character of the barrel 12 constricts to retain the components. Thus, to displace the needle carrier 14, i.e. disengage the first and third retention structures, a first axial displacement force is required. This force may act to locally expand the barrel 12 or, if the barrel 12 is rigid, compress the first portion 32 of the needle carrier 14 or both. In a preferred embodiment the interference retention of the needle carrier 14 in the barrel 12 is with a force $F_1$ greater than that required for insertion of the needle into a medicine vial, patient or other intended use. That is, during aspiration, the needle carrier 14 remains retained by the engagement of the first and third retention structures.

As manufactured, the plunger 16 is retained in the barrel 12 for example in the position as suggested in FG 7 in readiness for aspiration of medicine into the syringe 10.

The needle 42 is threaded onto the needle carrier 14, also as suggested in FIG. 7. The needle carrier 14 is retained against rotation during the mounting of the needle 42 by the coupling between the shoulder teeth 26 and the teeth of the surface 40. Once the needle 42 is secured to the needle carrier 14, the needle 42 is inserted into a medicine vial, for example, and the plunger 16 is withdrawn in the barrel 12 to aspirate medicine into the barrel 12. The seals 60a, b seal the plunger head 58 within the barrel 12. Any air remaining in the barrel 12 is aspirated from the barrel 12 by forward movement of the plunger 16.

The needle 42 is then inserted into the patient and the medicine is aspirated from the barrel 12 by forward motion of the plunger 16 and injected into the patient. The elastomeric character of the barrel 12 helps seal against the plunger 16. At the end of the injection, the plunger 16 is displaced to cause the head 58 to approach the needle carrier 14. The disk 64 deforms to pass through the neck 47 and ultimately snap outward to engage into the slots 80 of the wings 78 to thereby attach the needle carrier 14 to the plunger 16 as shown in FIG. 8. The stop 63 engages the needle carrier 14 to limit and guide the insertion of the head 58 components into the recess 72. The plunger 16 may then be withdrawn with a force greater than $F_1$ to overcome the retention force offered by the engagement by first and third retention structures 28, 32 to dislodge the needle carrier 14 for withdrawal into the barrel 12. Continued withdrawal of the plunger 16 pulls the needle carrier 14 into the barrel 12. When the second retention structure 30 is engaged by the third retention structure 34 of the needle carrier 14, the needle carrier 14 is retained within the barrel 12. With the needle carrier 14 in the withdrawn position, the needle 42 is nested within the barrel 12 from the open forward end 18 preventing inadvertent sticks by the needle 42.

As can be appreciated, the force $F_2$ necessary to separate the plunger from the needle carrier 14 must be greater than $F_1$ in order for the plunger to withdraw the needle carrier 14.

To re-use the syringe, it would be sterilized by suitable means such as an autoclave (steam or suitable gas) and the plunger would be re-positioned to locate the needle carrier 14 such that the first and third retention structures engage as do the teeth 26 and 43. The needle 42 is removed. The needle holder nipple 44 is held while the plunger is withdrawn with a force sufficient to overcome force F2 thereby releasing the plunger 16 from the needle carrier 14 for re-use thereof.

It should be noted that the present invention is subject to many modifications without departing from scope of the invention as expressed in the claims. For example, the barrel 12 need not be cylindrical. Further, only a portion of the barrel 12 may be elastomeric or coated with an elastomeric liner.

I claim:

1. A safety syringe comprising:
a hollow barrel having a forward and a rear end, said barrel including proximate the forward end a first retention structure and a first coupling structure and proximate said rear end a second retention structure;
a needle carrier disposed at said forward end and including (i) a third retention structure engaging the first retention structure to releaseably retain the needle carrier at said forward end and to engage the second coupling structure to retain said needle carrier in the barrel, (ii) a second coupling structure to engage the first coupling structure to prevent rotation of the needle carrier at said forward end, (iii) a mounting for mounting a needle and (iv) a first attachment component disposed opposite said mounting; and a plunger having a head to slideably seal within the barrel for aspiration of fluid into or displacement of fluid out of the barrel and a second attachment component to engage the first attachment component of the needle carrier to attach the needle carrier to said head, withdrawal of the plunger disengaging the third retention structure from the first retention structure to release the needle carrier and needle to be withdrawn to a position in the barrel where the third retention structure engages the second retention structure to retain the needle carrier and needle in the withdrawn position.

2. The safety syringe of claim 1 comprising said first and second retention structures include radial projections in said barrel and said third retention structure includes a cooperative radial depression in said needle carrier to receive said projections.

3. The safety syringe of claim 2 comprising said first and second retention structures include radially projecting ridges and said third retention structure includes a radial groove in said needle carrier.

4. The safety syringe of claim 1 comprising said first and second retention structures include grooves in said barrel and said third retention structure includes a radial protuberance to engage into said grooves.

5. The safety syringe of claim 1 comprising said barrel is constructed from an elastomeric material.

6. The safety syringe of claim 1 comprising said first and second attachment components includes a deformable tab snap-engaging a cooperative recess.

7. The safety syringe of claim 1 comprising said mounting is a luer lock mounting.

8. The syringe of claim 1 comprising said first and third retention structures cooperating to release the needle carrier at a first withdrawal force and said second and third retention structures cooperating to release the needle carrier at a greater, second withdrawal force.

9. A safety syringe comprising:

a hollow cylindrical barrel having a forward and a rear end, said barrel including proximate the forward end a first radial projection and a first coupling structure and proximate said rear end a second radial projection;

a needle carrier disposed at said forward end and including (i) a depression to receive the first radial projection to releaseably retain the needle carrier at said forward end and to receive the second radial projection to retain said needle carrier in the barrel, (ii) a second coupling structure to engage the first coupling structure to prevent rotation of the needle carrier at said forward end, (iii) a mounting for mounting a needle and (iv) a first attachment component disposed opposite said mounting; and a plunger having a head to slideably seal within the barrel for aspiration of fluid into or displacement of fluid out of the barrel and a second attachment component to engage the first attachment component of the needle carrier to attach the needle carrier to said head, withdrawal of the plunger disengaging the first radial projection from the depression to release the needle carrier and needle to be withdrawn to a position in the barrel where the second radial projection engages the depression to retain the needle carrier and needle in the withdrawn position.

10. A safety syringe comprising:

a hollow barrel having a forward and a rear end, said barrel including proximate the forward end a first groove and a first coupling structure and proximate said rear end a second groove;

a needle carrier disposed at said forward end and including (i) a protuberance to engage into the first groove to releaseably retain the needle carrier at said forward end and to engage into the second groove to retain said needle carrier in the barrel, (ii) a second coupling structure to engage the first coupling structure to prevent rotation of the needle carrier at said forward end, (iii) a mounting for mounting a needle and (iv) a first attachment component disposed opposite said mounting; and a plunger having a head to slideably seal within the barrel for aspiration of fluid into or displacement of fluid out of the barrel and a second attachment component to engage the first attachment component of the needle carrier to attach the needle carrier to said head, withdrawal of the plunger disengaging the protuberance from the first groove to release the needle carrier and needle to be withdrawn to a position in the barrel where the protuberance engages the second groove to retain the needle carrier and needle in the withdrawn position.

* * * * *